United States Patent [19]

Hasegawa et al.

[11] Patent Number: 4,975,517

[45] Date of Patent: Dec. 4, 1990

[54] POLYAMIDE FROM OPTICALLY ACTIVE, ANTI HEAD-TO-HEAD COUMARIN DIMER

[75] Inventors: Masaki Hasegawa, Tokyo; Kazuhiko Saigou, Souka; Noriyuki Yonezawa, Tokyo; Toshio Kanoe, Fuji; Kazuhiro Sekimoto, Kimitsu, all of Japan

[73] Assignee: Masaki Hasegawa, Tokyo, Japan

[21] Appl. No.: 30,232

[22] Filed: Mar. 26, 1987

Related U.S. Application Data

[63] Continuation of Ser. No. 793,069, Oct. 4, 1985, abandoned.

[51] Int. Cl.$^5$ ............................................. C08G 69/26
[52] U.S. Cl. ................................... 528/185; 528/346; 528/347; 528/348; 528/354
[58] Field of Search ............... 528/185, 347, 346, 348, 528/354

[56] References Cited

PUBLICATIONS

Chemical Abstracts, vol. 79; 1973; 5665 m (Suzuki et al.).
Chemical Abstracts, vol. 97; 1982, 56330 c (Hasegawa et al.).
Chemical Abstracts, vol. 99; 1983, 123078 h (Hasegawa et al.).

Primary Examiner—Harold D. Anderson
Attorney, Agent, or Firm—Birch, Stewart, Kolasch & Birch

[57] ABSTRACT

A racemic, anti head-to-head coumarin dimer can be separated into its optically active constituents by using an optically active amine. Each optically active isomer can be further reacted with a diamine to afford an optically active polyamide.

2 Claims, No Drawings

POLYAMIDE FROM OPTICALLY ACTIVE, ANTI HEAD-TO-HEAD COUMARIN DIMER

This application is a continuation of copending application Ser. No. 793,069, filed on Oct. 4, 1985 now abandoned.

FIELD OF THE INVENTION

The present invention relates to an optically active, anti head-to-head coumarin dimer of the following formula (I) or (II):

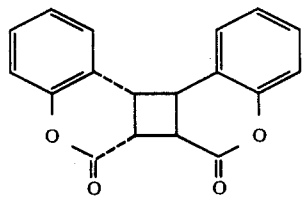

(I)

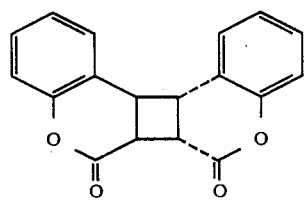

(II)

These two optically active isomers are hereinafter referred to as the (+)-dimer and the (−)-dimer, respectively.

Further, the present invention relates to a novel optically active polyamide which corresponds to a derivative of the optically active, anti head-to-head coumarin dimer.

BACKGROUND OF THE INVENTION

The anti head-to-head coumarin dimer can be obtained by photodimerizing coumarin.

This compound is optically inactive, i.e. a (±)-dimer. Since the dimer contains two lactone rings which are highly reactive and further a cyclobutane ring which can be cleaved by light, the compound is useful even in the form of the (±)-dimer as a starting material for the production of photopolymers. The (+)- or (−)-dimer which has an optical activity in addition to high reactivity can be more widely used. For example, the lactone ring is reacted with a hydroxyl or amino group to form a ring-opening compound which can be then ring-closed on heating to reform the original dimer, so that the dimer can be used in the optical resolution of compounds containing these reactive functional groups.

Derivatives of the (+)- or (−)-dimer are also very useful. For example, they are easily reacted with polyhydric alcohols or polyamines to form polyesters or polyamides, and the obtained optically active polymers can be used in asymmetric synthesis, optical resolution, analysis, etc.

Further, the present inventors have found that when the obtained optically active isomer, i.e. (+)- or (−)-dimer, is reacted with a diamino compound, a novel optically active polymer can be obtained. The present invention is based on these findings.

SUMMARY OF THE INVENTION

The present invention provides an optically active, anti head-to-head coumarin dimer of the following formula (I) or (II):

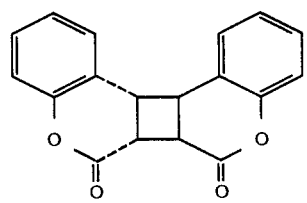

(I)

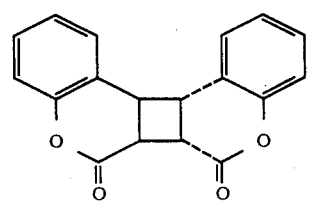

(II)

Further, the present invention provides a process for preparing an optically active, anti head-to-head coumarin dimer of the following formula (I) or (II):

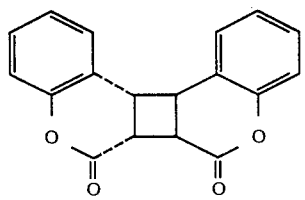

(I)

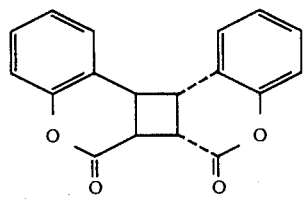

(II)

characterized by separating a diamide derived from the racemic, anti head-to-head coumarin dimer and an optically active amine into diastereomers, deaminating each of the diastereomers and ring-closing each of the deaminated products.

DETAILED DESCRIPTION OF THE INVENTION

The method for obtaining the optically active dimer of the present invention is characterized in that a diamide derived from the racemic, anti head-to-head coumarin dimer and an optically active amine is resolved into diastereomers, each diastereomer is deaminated and each of the deaminated products is ring-closed. The method involves steps represented by the following formulae:

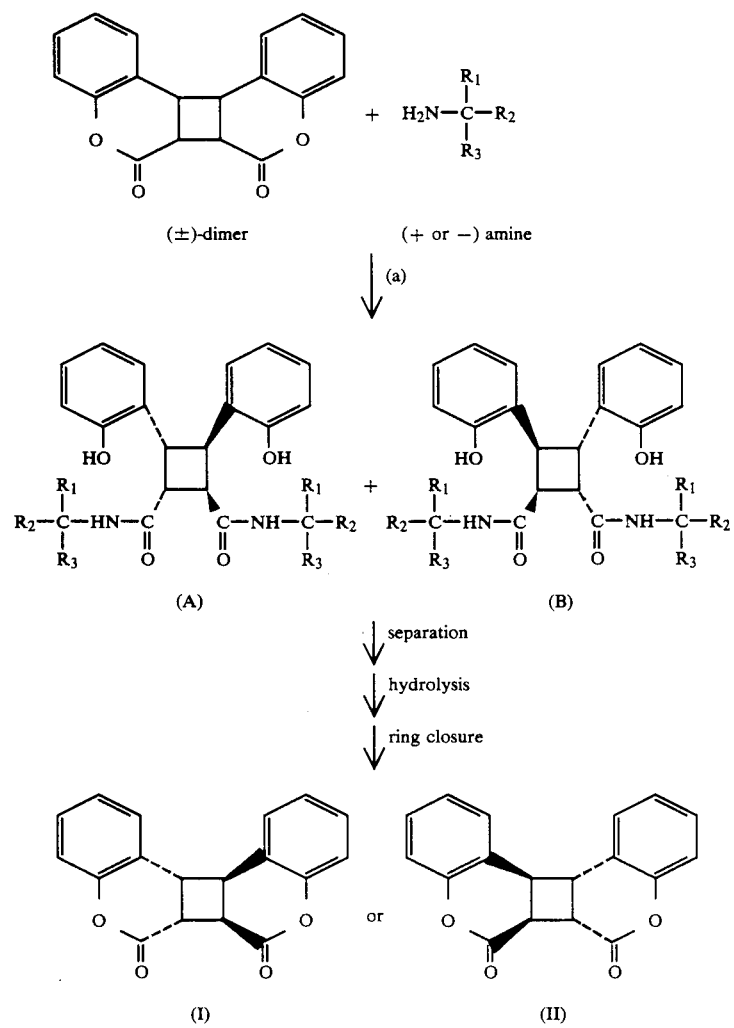

The amidation reaction (a) readily proceeds when the dimer is mixed and reacted with the optically active amine in a solvent such as dioxane.

The amides (A) and (B) are diastereomers and differ in solubility from each other. Therefore, when the reaction is carried out in an appropriate solvent under specified conditions, it is possible to precipitate and separate only one diastereomer as the reaction proceeds. For example, when (−)-1-phenylethylamine is used as the amine, the amide derived from the (+)-dimer is difficultly soluble in dioxane, while the one derived from the (−)-dimer is easily soluble.

Amino acid derivatives, alkaloid derivatives, etc., can also be used as the amine in the present invention.

The amide which is separated and purified by an appropriate method such as recrystallization can be hydrolyzed by any of the conventional methods. For example, a method using alcoholic HCl is preferred.

The hydrolyzate is ring-closed by a conventional lactonization method as such or, if necessary, after purification. For example, the ring closure is readily effected by heating in acetic acid under reflux to form the (+)- or (−)-dimer.

The polyamide of the present invention is different in optical properties as well as solubility, thermal properties, etc. from the corresponding racemic polyamide.

The polyamide of the present invention contains highly reactive phenol groups in the molecule and the optical activity has a characteristic originating from the cyclobutane ring, so that the polyamide itself or its derivative which has a substituted phenol group or in which part of the cyclobutane rings are cleaved is a material suitable for use in asymmetric synthesis, optical resolution analysis, etc.

The optically active polyamides of the present invention can be represented by the following formulae:

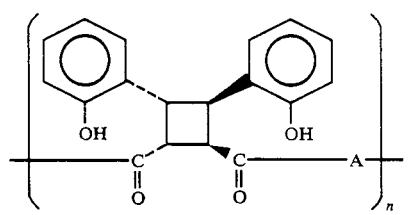

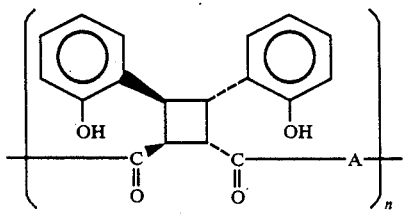

wherein A is a residue formed by removing one active hydrogen atom from each of two amino groups of a primary or secondary diamine. The diamine may be saturated or unsaturated and may be a mixture of two or more diamines or modified with a triamine or the like.

The polymer chain is usually terminated with either a hydrogen atom or the above dimer (I) or (II), and sometimes with an impurity. The polymers of the present invention are polycondensates, and n in the above formula is at least 2, preferably from 2 to 1000.

Examples of residue A in the above formula are as follows:

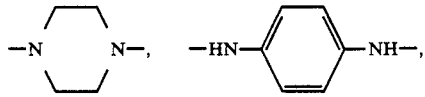

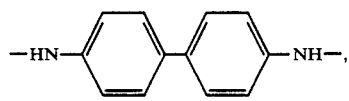

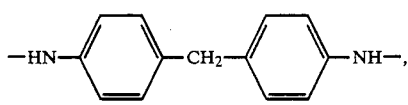

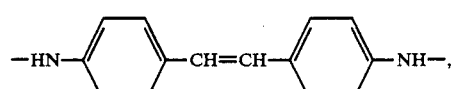

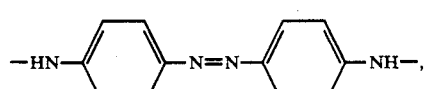

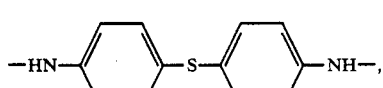

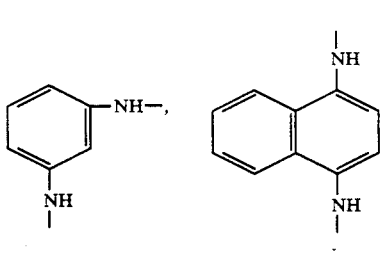

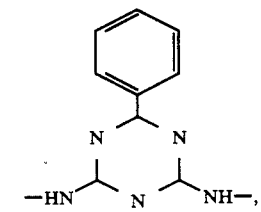

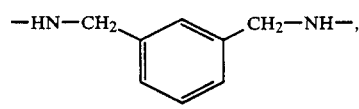

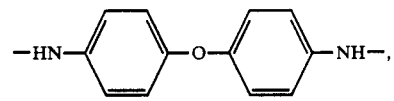

The optically active polyamide of the present invention can be easily obtained by reacting the (+) or (−) anti head-to-head coumarin dimer with the corresponding diamine. Usually, the reaction proceeds in the absence of a specific catalyst. Preferably, both reactants in equimolar quantities are reacted in an aprotic polar solvent. Preferred examples of the solvents include dimethylacetamide, dioxane, methylpyrrolidone, dimethyl sulfoxide and hexamethyl phosphoric triamide.

When the coumarin dimer and the diamine are used in a molar ratio of 1:1 in the above polymerization reaction, a polymer having a relatively high degree of polymerization can be obtained, while when the molar ratio is changed or a monofunctional compound such as a monoamine is added, a polymer having a relatively low degree of polymerization can be obtained.

The following examples will further illustrate the present invention.

EXAMPLE 1

58.46 g of the (±)-dimer is dissolved in 850 ml of dioxane. 48.47 g of (−)-1-phenylethylamine is added dropwise thereto while stirring over a period of 30 min. After stirring for 12 hr, the precipitate is separated by filtration, washed with dioxane and dried at 60° C. in vacuo to afford 42.29 g of a crystal.

The product is diamide (A) derived from the (+)-dimer and the yield was 39.5%.

After the filtrate is concentrated, 150 ml of acetone and 150 ml of methanol are added thereto and the mixture is dissolved by heating and left to stand at 5° C. for 12 hr.

The precipitated crystal is dried to afford 35.54 g (yield 33.3%) of the diamide (B) derived from the (−)-dimer.

The properties of these diamides A and B are shown in Table 1.

TABLE 1

| | Melting point (°C.) | $[\alpha]_D^{21(*)}$ | | Elemental analysis (calcd.) (%) | |
|---|---|---|---|---|---|
| Diamide A | 237–238 | −19.0° | C | 76.54 | (76.38) |
| | | | H | 6.27 | (6.40) |
| | | | N | 5.17 | (5.23) |
| Diamide B | 246–247 | −177.3° | C | 76.66 | (76.38) |
| | | | H | 6.16 | (6.40) |

TABLE 1-continued

| | Melting point (°C.) | $[\alpha]_D^{21(*)}$ | Elemental analysis (calcd.) (%) | |
|---|---|---|---|---|
| | | | N | 5.19 (5.23) |

(*)c 0.5, 99% methanol

EXAMPLE 2

5,346.5 mg of the diamide of the (−)-dimer is added to a mixture of 100 ml of 99% ethanol and 50 ml of concentrated hydrochloric acid, and the mixture is refluxed.

After 20 hr, the reflux is terminated and the mixture is concentrated to remove ethanol. 200 ml of water is added thereto and the mixture is extracted three times with ethyl acetate (each 150 ml).

After ethyl acetate is removed, 150 ml of acetic acid is added and the mixture is refluxed.

The resulting material is developed on a silica gel column (Wakogel C-200, 4φ×15 cm) eluting with 500 ml of benzene and then 500 ml of a mixture of benzene and ethyl acetate (90:10) successively to afford 2451.9 mg (yield 83.9%) of the crude (−)-dimer crystal. This crude crystal is recrystallized from a solvent mixture of ethyl acetate and hexane (2:3) to afford 1.92 g (yield 65.7%) of the (−)-dimer.

EXAMPLE 3

The diamide of the (+)-dimer is treated in a similar manner to that described in Example 2 to afford the (+)-dimer in a yield of 63.4%.

The properties of these (+)- and (−)-dimers as well as those of the (±)-dimer as a reference are shown in Table 2.

TABLE 2

| | Melting point (°C.) | $[\alpha]_D^{21\,(*)}$ | $[\alpha]_{435}^{21(*)}$ |
|---|---|---|---|
| (+)-Dimer | 168–169 | +9.0° | +66.0 |
| (−)-Dimer | 168.5–169 | −9.0° | −65.8 |
| (±)-Dimer | 187.5–189 | — | — |

EXAMPLE 4

0.2552 g (0.9 mmol) of the (−) anti head-to-head coumarin dimer and an equimolar quantity of p-phenylenediamine are dissolved in 1.7 ml of dimethylacetamide and left to stand at 80° C. for 24 hr.

After the completion of the reaction, the product is added dropwise to methanol to afford a polymer (yield 87%).

The resulting polymer had a reduced viscosity of 0.36 (0.3 g/dl in dimethylacetamide at 30° C.) and the optical activity was $[\alpha]_D = -89.4°$ and $[\alpha]_{435} = -260.0°$ (0.5 g/100 ml in dimethylacetamide).

EXAMPLE 5

The procedure of Example 4 is repeated except that 0.8 mmol of hexamethylenediamine was used as the diamine and the reaction is carried out in 1.6 ml of dimethylacetamide.

The yield and the properties of the product are shown in Table 3.

EXAMPLE 6

2.1 mmol of m-xylylenediamine is used and the reaction is carried out in 4.3 ml of dimethylacetamide in a similar manner to that described above.

The yield and the properties are shown in Table 3.

EXAMPLE 7

1 mmol of 4,4′-diaminodiphenyl ether is used and the reaction is carried out in 2.0 ml of dimethylacetamide in a similar manner to that described above.

The yield and the properties are shown in Table 3.

EXAMPLE 8

1 mmol of piperazine is used and the reaction is carried out in 2.1 ml of dimethylacetamide in a similar manner to that described above.

The yield and the properties are shown in Table 3.

TABLE 3

| Example No. | Diamine | Yield (%) | Reduced[a] Viscosity | $[\alpha]_D$ | $[\alpha]_{435}$ |
|---|---|---|---|---|---|
| 5 | hexamethylenediamine | 86 | 0.68 | −59.0°[b] | −160.9°[b] |
| 6 | m-xylylenediamine | 86 | 0.63 | −26.8°[c] | −79.3°[c] |
| 7 | 4,4′-diaminodiphenyl ether | 65 | 0.31 | −91.6°[d] | −266.7°[d] |
| 8 | piperazine | 97 | 0.51 | +30.6°[c] | +45.4°[c] |

Note:
[a]in dimethylacetamide, 0.3 g/dl, 30° C.
[b]in dimethylacetamide, 0.49 g/dl
[c]in dimethylacetamide, 0.5 g/dl
[d]in dimethylacetamide, 0.51 g/dl

What is claimed is:

1. An optically active polyamide having repeating units (III) or (IV):

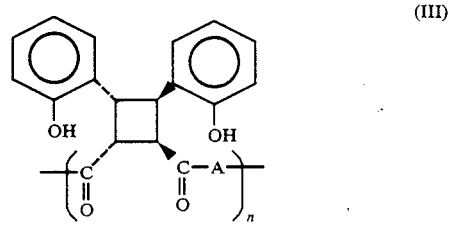

(III)

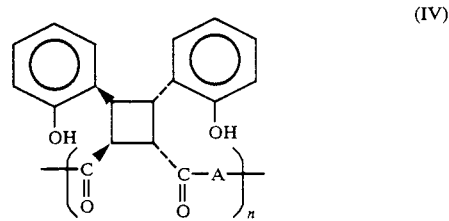

(IV)

in which A is a residue formed by removing one active hydrogen atom from each of two amino groups, wherein the residue A is:

and n is at least 2.
2. An optically active polyamide having repeating units (III) or (IV):
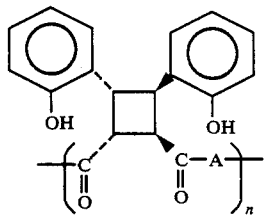
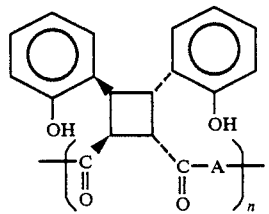
in which A is a residue formed by removing one active hydrogen atom from each of two amino groups, wherein the residue A is:
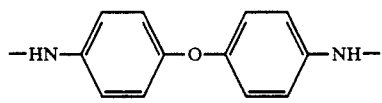
and n is at least 2.
* * * * *